United States Patent
Chomas et al.

(10) Patent No.: US 7,993,272 B2
(45) Date of Patent: Aug. 9, 2011

(54) IMAGE PLANE STABILIZATION FOR MEDICAL IMAGING

(75) Inventors: James E. Chomas, San Francisco, CA (US); Kutay F. Ustuner, Mountain View, CA (US); Thilaka S. Sumanaweera, Los Altos, CA (US)

(73) Assignee: Siemens Medical Solutions USA, Inc., Malvern, PA (US)

(*) Notice: Subject to any disclaimer, the term of this patent is extended or adjusted under 35 U.S.C. 154(b) by 205 days.

(21) Appl. No.: 12/239,996

(22) Filed: Sep. 29, 2008

(65) Prior Publication Data
US 2009/0054779 A1    Feb. 26, 2009

Related U.S. Application Data

(62) Division of application No. 10/696,608, filed on Oct. 29, 2003, now abandoned.

(51) Int. Cl.
*A61B 8/00* (2006.01)
(52) U.S. Cl. ........................... 600/437; 600/443
(58) Field of Classification Search ........... 600/437–447
See application file for complete search history.

(56) References Cited

U.S. PATENT DOCUMENTS

| | | | |
|---|---|---|---|
| 3,561,430 A | 2/1971 | Filler, Jr. et al. | |
| 4,625,555 A * | 12/1986 | Fujii | 73/597 |
| 4,722,345 A * | 2/1988 | Ueno et al. | 600/445 |
| 4,735,211 A | 4/1988 | Takasugi | |
| 5,255,680 A | 10/1993 | Darrow et al. | |
| 5,373,848 A * | 12/1994 | Melton et al. | 600/455 |
| 5,673,830 A | 10/1997 | Matthews | |
| 5,675,554 A | 10/1997 | Cole et al. | |
| 5,685,308 A | 11/1997 | Wright et al. | |
| 5,782,766 A * | 7/1998 | Weng et al. | 600/443 |
| 5,873,830 A | 2/1999 | Hossack et al. | |
| 5,876,342 A * | 3/1999 | Chen et al. | 600/443 |
| 5,899,861 A | 5/1999 | Friemel et al. | |
| 5,910,114 A | 6/1999 | Nock et al. | |
| 5,967,987 A * | 10/1999 | Sumanaweera et al. | 600/454 |
| 6,083,168 A * | 7/2000 | Hossack et al. | 600/443 |
| 6,086,535 A * | 7/2000 | Ishibashi et al. | 600/439 |
| 6,110,118 A * | 8/2000 | Guracar et al. | 600/453 |
| 6,132,376 A | 10/2000 | Hossack et al. | |
| 6,191,862 B1 | 2/2001 | Swanson et al. | |

(Continued)

OTHER PUBLICATIONS

U.S. Appl. No. 12/240,078, filed Sep. 29, 2008 with inventors Chomas et al.

(Continued)

*Primary Examiner* — Long V Le
*Assistant Examiner* — Sanjay Cattungal

(57) ABSTRACT

A medical imaging system automatically acquires two-dimensional images representing a user-defined region of interest despite motion. The plane of acquisition is updated or altered adaptively as a function of detected motion. The user-designated region of interest is then continually scanned due to the alteration in scan plane position. A multi-dimensional array is used to stabilize imaging of a region of interest in a three-dimensional volume. The user defines a region of interest for two-dimensional imaging. Motion is then detected. The position of a scan plane used to generate a subsequent two-dimensional image is then oriented as a function of the detected motion within the three-dimensional volume. By repeating the motion determination and adaptive alteration of the scan plane position, real time imaging of a same region of interest is provided while minimizing the region of interest fading into or out of the sequence of images.

18 Claims, 2 Drawing Sheets

U.S. PATENT DOCUMENTS

| | | |
|---|---|---|
| 6,222,948 B1 | 4/2001 | Hossack et al. |
| 6,234,968 B1 | 5/2001 | Sumanaweera et al. |
| 6,254,539 B1 | 7/2001 | Pang et al. |
| 6,277,074 B1 * | 8/2001 | Chaturvedi et al. ............ 600/437 |
| 6,280,402 B1 * | 8/2001 | Ishibashi et al. .................. 601/2 |
| 6,299,573 B1 | 10/2001 | Hull, Jr. et al. |
| 6,299,579 B1 | 10/2001 | Peterson et al. |
| 6,306,091 B1 | 10/2001 | Sumanaweera et al. |
| 6,334,846 B1 * | 1/2002 | Ishibashi et al. ............... 600/439 |
| 6,352,508 B1 | 3/2002 | Pang et al. |
| 6,360,027 B1 | 3/2002 | Hossack et al. |
| 6,442,289 B1 | 8/2002 | Olsson et al. |
| 6,464,642 B1 | 10/2002 | Kawagishi |
| 6,527,717 B1 * | 3/2003 | Jackson et al. ................ 600/437 |
| 6,560,375 B1 | 5/2003 | Hathaway et al. |
| 6,589,176 B2 | 7/2003 | Jago et al. |
| 6,606,456 B2 | 8/2003 | Fujinaga |
| 6,618,197 B1 | 9/2003 | Hayakawa |
| 6,659,953 B1 | 12/2003 | Sumanaweera et al. |
| 6,684,098 B2 * | 1/2004 | Oshio et al. ................... 600/429 |
| 6,733,458 B1 * | 5/2004 | Steins et al. ................... 600/461 |
| 6,755,787 B2 * | 6/2004 | Hossack et al. ................ 600/447 |
| 6,824,514 B2 * | 11/2004 | Poland et al. .................. 600/437 |
| 6,976,961 B2 * | 12/2005 | Jackson et al. ................ 600/443 |
| 7,150,716 B2 | 12/2006 | Jones et al. |
| 7,530,951 B2 * | 5/2009 | Fehre et al. .................... 600/459 |
| 2001/0020127 A1 * | 9/2001 | Oshio et al. ................... 600/429 |
| 2002/0159769 A1 | 10/2002 | Fujinaga |
| 2002/0186970 A1 * | 12/2002 | Hirano ............................. 396/52 |
| 2003/0097068 A1 * | 5/2003 | Hossack et al. ................ 600/443 |
| 2003/0105401 A1 | 6/2003 | Jago et al. |
| 2004/0019447 A1 | 1/2004 | Shachar |
| 2004/0064036 A1 * | 4/2004 | Mao et al. ...................... 600/413 |
| 2004/0073111 A1 * | 4/2004 | Poland et al. .................. 600/437 |
| 2004/0220476 A1 * | 11/2004 | Fehre et al. .................... 600/459 |
| 2005/0096538 A1 | 5/2005 | Chomas |
| 2005/0096589 A1 | 5/2005 | Shachar |

OTHER PUBLICATIONS

U.S. Appl. No. 12/240,153, filed Sep. 29, 2008 with inventors Chomas et al.

* cited by examiner

IMAGE PLANE STABILIZATION FOR MEDICAL IMAGING

RELATED APPLICATIONS

The present patent document is a divisional of U.S. Publication No. 2005/0096538, published on May 5, 2005, (Ser. No. 10/696,608), filed Oct. 29, 2003, now abandoned which is hereby incorporated by reference.

BACKGROUND

The present invention relates to image stabilization in medical imaging. An imaging position is stabilized with respect to a region of interest as images are acquired over time.

In medical diagnostic ultrasound imaging, a transducer is positioned adjacent to a patient. The sonographer attempts to maintain the transducer in a given position relative to a region of interest within the patient. Temporal variations in the transducer position due to movements by the sonographer, movements by the patient, breathing motion, heart motion or other sources of motion cause the transducer to move relative to the patient. The scan plane is typically fixed at least in the elevation dimension with respect to the transducer. The undesired or unintended motion results in scanning different tissue within the patient.

Images may be stabilized within the scan plane. Motion between subsequent images in a sequence of images is tracked. The acquired image data is then adjusted or shifted along the azimuth or range dimensions so that a region of interest is maintained at the same location on the display. Other processes, such as contrast agent quantification, use motion tracking to reduce motion artifacts. Previously acquired data is processed or shifted as a function of the motion to reduce the artifacts. However, some motion artifacts may remain despite shifts in data. The shifted data may not optimally represent the region of interest. To provide the maximum versatility, a large amount of unused image information is acquired and stored for allowing shifts. Acquiring lots of ultrasound information may reduce frame rates.

Motion tracking is also used in three-dimensional and extended field of view imaging. A plurality of two-dimensional scans are performed in different positions within a same plane for extended field of view imaging. The motion between the various acquired images is determined for assembling the images together in an extended field of view. Similarly for three-dimensional imaging, a plurality of two-dimensional images are acquired for a plurality of scan planes within a three-dimensional volume. Motion tracking is performed using ultrasound data, motion sensors on the transducer or other techniques for determining the relative positions of the scan planes. An image representing three-dimensional space is then rendered from the acquired sets of ultrasound data. However, multiple images or sets of data are acquired to form the extended field of view or three-dimensional representation.

Another motion adaptive process is disclosed in U.S. Pat. No. 5,873,830. An amount of motion between different images is detected. Where motion is not detected or minimal, the beamformer is configured to increase spatial resolution, such as by increasing line density or the number of transmit beams. Where motion is detected, the frame rate is increased by decreasing the line density or number of beams. However, changing density or number of beams as a function of detected motion may still result in desired tissue fading in or fading out of the image scan plane due to the motion.

BRIEF SUMMARY

By way of introduction, the preferred embodiments described below includes methods and systems for stabilizing a scan plane in medical imaging. A medical imaging system automatically acquires two-dimensional images representing a user-defined region of interest despite motion. The plane of acquisition is updated or altered adaptively as a function of detected motion. The user-designated region of interest is then continually scanned due to the alteration in scan plane position.

In one embodiment, a multi-dimensional array is used to stabilize imaging of a region of interest in a three-dimensional volume. The user defines a region of interest for two-dimensional imaging. Motion is then detected for six or other number of degrees of freedom, such as translation along each of three dimensions and rotation about each of those three dimensions. The position of a scan plane used to generate a subsequent two-dimensional image is then oriented as a function of the detected motion within the three-dimensional volume. The scan plane is positioned such that the region of interest designated by the user is within the scan plane. By repeating the motion determination and adaptive alteration of the scan plane position, real time imaging of a same region of interest is provided while minimizing the region of interest fading into or out of the sequence of images.

In a first aspect, a method for stabilizing an image plane in medical imaging is provided. Motion is tracked within a region. An acquisition scan plane position is automatically altered relative to the transducer as a function of the motion.

In a second aspect, a method for stabilizing a scan plane within a volume in medical diagnostic ultrasound imaging is provided. A region of interest is identified. Data representing at least portions of a three-dimensional volume positioned at least partially around the region of interest is acquired. Data representing sub-volumes of the three-dimensional volume is acquired using fewer scan lines. The data representing the sub-volumes is compared with the data representing the portions of the three-dimensional volume. Motion is detected as a function of the comparison. A two-dimensional scan plane is positioned within the three-dimensional volume as a function of the region of interest and the detected motion. A two-dimensional image is then acquired using the positioned two-dimensional scan plane.

In a third aspect, a method for stabilizing imaging within a volume in medical diagnostic ultrasound imaging is provided. A two-dimensional area is repetitively scanned with a multi-dimensional transducer array. Motion within a volume that includes the two-dimensional area is repetitively detected. The two-dimensional area is adaptively repositioned within the volume as a function of the detected motion.

In a fourth aspect, a system for stabilizing a scan plane within a volume in medical imaging is provided. A multi-dimensional transducer array connects with a beamformer. The beamformer is responsive to a beamformer controller and is operable to acquire data representing tissue within a data acquisition scan plane. The beamformer controller is operable to control a position of the data acquisition scan plane relative to the multi-dimensional transducer array. A processor is operable to detect motion within a volume. The beamformer controller is operable to alter the position of the data acquisition scan plane in response to the detected motion.

The present invention is defined by the following claims, and nothing in this section should be taken as a limitation on those claims. Further aspects and advantages of the invention are discussed below in conjunction with the preferred embodiments.

BRIEF DESCRIPTION OF THE DRAWINGS

The components and the figures are not necessarily to scale, emphasis instead being placed upon illustrating the principles of the invention. Moreover, in the figures, like reference numerals designate corresponding parts throughout the different views.

DETAILED DESCRIPTION OF THE DRAWINGS AND PRESENTLY PREFERRED EMBODIMENTS

Image movement due to respiratory motion, patient motion, sonographer motion or other undesirable motions leading to a tissue of interest moving into and/or out of a sequence of images is avoided. By tracking a position of a tissue of interest, subsequent acquisitions are aligned to insonnify the tissue, resulting in a steady or more stable maintenance of the image plane relative to the tissue of interest. In addition to ease of use and general aesthetic desirability, quantification is made more stable and consistent. Diagnosis may be improved since each image in the sequence is more likely to represent the tissue of interest. Moving tissues, such as associated with the fetus or cardiology imaging may be more accurately monitored by maintaining a scan plane relative to the moving tissue despite the tissue movement. Perfusion measurements, such as associated with contrast agent enhancement applications, may be improved.

Figure 1:
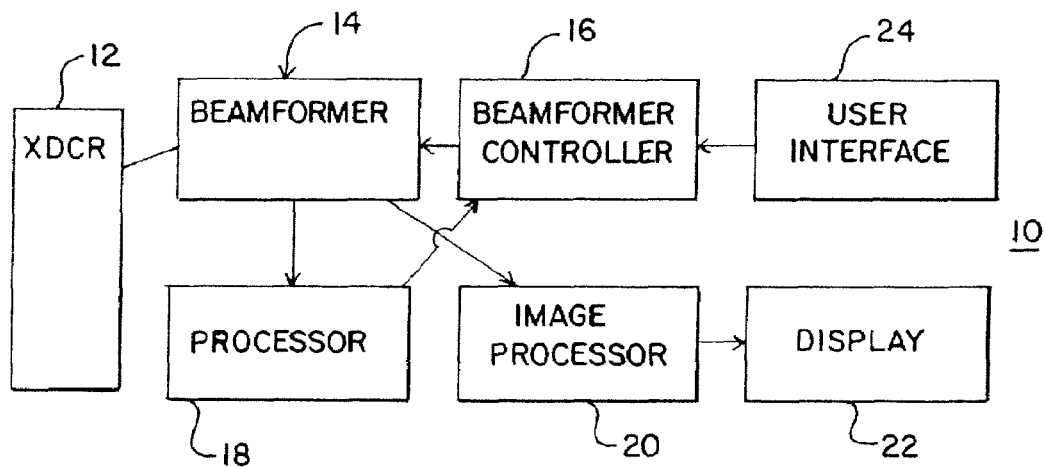
FIG. 1 is a block diagram of one embodiment of a system for stabilizing a scan plane in medical imaging.

FIG. 1 shows one embodiment of a medical imaging system 10 for stabilizing a scan plane within a region or volume. The system 10 includes a transducer 12, a beamformer 14, a beamformer controller 16, a processor 18, an image processor 20, a display 22 and a user interface 24. Additional, different or fewer components may be provided, such as not having the user interface 24, image processor 20 or display 22. In one embodiment, the system 10 is a medical diagnostic ultrasound system for acquiring image information using acoustic energy. In alternative embodiments, other medical imaging systems may be used, such as a computed tomography, magnetic resonance, X-ray or other now known or later developed imaging systems. Using feedback from received data to the scanner, such as the ultrasound beamformer 14 used for acquisition, the position of a subsequent scan is controlled to maintain a tissue of interest within the scan plane or acquisition region.

The transducer 12 is a multi-dimensional array of elements. For example, a 1.5, 1.75 or two-dimensional array of elements are provided. Annular, wobbler, or other mechanically or electrically steerable arrays may be used. Two-dimensional array is used broadly to include an array of N×M elements where N and M are equal or non-equal, but both greater than 1. Arrays with non-square or non-rectangular element patterns may be provided in any multi-dimensional arrangement. The multi-dimensional transducer array 12 is steerable in two dimensions, such as along an elevation and azimuth dimension. In alternative embodiments, the transducer 12 is a one-dimensional linear array for scanning a two-dimensional region.

The beamformer 14 is an analog or digital ultrasound transmit and/or receive beamformer. In one embodiment, the beamformer 14 is the beamformer disclosed in U.S. Pat. Nos. 5,675,554 and 5,685,308, the disclosures of which are incorporated herein by reference. The beamformer 14 is shown in general, but in one embodiment includes both a transmit and receive beamformers as separate devices. The transmit beamformer generates the acoustic energy along the acquisition scan plane. The receive beamformer receives responsive echo signals and provides them to the image processor 20 and the processor 18.

In one embodiment, sufficient beamformer channels are provided on transmit and/or receive to beamform along both the azimuth and elevation dimensions. To reduce the number of beamformer channels, sparse array techniques may be used. Alternatively, plane wave imaging techniques are provided. In yet another alternative embodiment, the number of cables between the transducer 12 and the beamformer 14 is reduced by time division multiplexing for allowing a greater number of channels while minimizing the size of the cable. In yet another alternative embodiment, sufficient channels are provided for beamforming along an azimuth dimension, and switchable connections between the channels and elements of the arrays are used to position a linear array of elements along any of azimuth and elevation positions on the plane of the transducer 14. As a result, an acquisition scan plane is always normal to at least one dimension but electronic steering is provided for scanning along angles for another dimension.

In one embodiment, the beamformer 14 includes a plurality of transmit channels connectable with one or more of the elements of the transducer 12. Each transmit channel includes a delay, amplifier and a waveform generator. Additional, different or fewer components may be provided. The transmit channels generate waveforms with different apodization and delay profiles relative to other waveforms for steering acoustic energy along one or more scan lines. By selecting which transmit channels connect to which elements of the transducer array 12, ultrasound scan lines are generated along any various azimuthal and elevation locations and angles.

The beamformer 14 is responsive to the beamformer controller 16 for positioning the acquisition scan plane. Using the above-described electronic, mechanical or both electronic and mechanical steering, the acquisition scan plane is positioned within a two-dimensional or three-dimensional region. Acoustic energy is transmitted in any of various now known or later developed scan patterns along the scan plane for acquiring data. The acquisition scan plane is used for acquiring data for subsequent images.

As part of a feedback control loop, the processor 18 is a digital signal processor, general processor, application specific integrated circuit, control processor, detector or other now known or later developed processor. In one embodiment, the processor 18 is a separate component from the beamformer 14, the beamformer controller 16 and the image processor 20. For example, the processor 18 is a general, system control processor connected with the user interface 24. In other embodiments, the processor 18 is a processor within the beamformer 14, the beamformer controller 16 or the image processor 20. In yet other embodiments, the processor 18 has multiple processors or circuits distributed at a same or different locations throughout the system 10. The processor 18 is operable to detect motion within a volume in response to acquired data. The processor 18 identifies motion from the received ultrasound data. While the processor 18 is shown connected to the beamformer 14, in other embodiments, the processor 18 connects to an output of the image processor 20 for processing detected data.

The beamformer controller 16 is a general processor, application specific integrated circuit, digital signal processor or other now known or later developed controller for controlling the beamformer 14. In one embodiment, the beamformer controller 16 is the controller disclosed in U.S. Pat. No. 5,675,554 or 5,685,308. The beamformer controller 16 is operable to control a position of the data acquisition scan plane relative to the multi-dimensional transducer array 12. The beamformer controller 16 receives input from the processor 18. The input indicates a desired scan plane position, an amount of motion, a direction of motion, or change. In response to the detected motion provided by the processor 18 or calculated by the beamformer controller 16, the beamformer controller 16 is operable to alter the position of the data acquisition scan plane for transmit and/or receive operation. For example, the beamformer controller 16 controls the apodization and delay profile generated across the multiple channels of the transmit beamformer 14. The connection of the channels to specific elements within the array may also be controlled by the beamformer controller 16, such as by controlling a multiplexer or transmit and receive switch. As a result, the scan plane is positioned at any of various positions and angles within three-dimensional space relative to the transducer 12.

The image processor 20 includes one or more spatial or temporal filters, one or more detectors and a scan converter. Additional, different or fewer components may be provided. The image processor 20 receives data responsive to transmission along the acquisition scan plane. The data is then detected and converted to a display format. A resulting image is displayed on the display 22. The detected information or image information may alternatively or additionally be stored for later viewing or processing. In one embodiment, the image processor 20 is operable to determine one or more quantities as a function of the data, such as a distance between detected data points associated with tissue features. Since the feedback between the beamformer 14, the processor 18 and the beamformer controller 16 provides for real time or adaptive positioning of the acquisition scan plane, the resulting images generated by the image processor are more likely images of a tissue of interest despite undesired motions.

The user interface 24 is a keyboard, trackball, mouse, touchpad, touch-screen, slider, knob, button, combinations thereof or other now known or latter developed input device. The user interface 24 is shown connected with the beamformer controller 16. In alternative embodiments, the user interface 24 connects to the beamformer controller 16 through one or more other devices, such as the processor 18 or a system control processor. The user designates a region of interest within a two-dimensional or three-dimensional image using the user interface 24. The user interface 24 is operable to receive the input indicating a region of interest and store or otherwise communicate the spatial position within the image to the beamformer controller 16 or processor 18. For example, a plurality of two-dimensional images are generated. Once the user positions the transducer 12 such that a tissue of interest is being imaged, the user indicates the position of the tissue of interest, such as by tracing the tissue of interest or starting an automatic border detection function. Alternatively, the tissue of interest may be automatically set by the system using techniques such as automatic image segmentation.

Once a region of interest is identified by the user, the system 10 tracks motion of the transducer 12 relative to the tissue of interest within a three dimensional volume. As the region of interest moves relative to the transducer 12 due to undesired motion, the acquisition scan plane is altered to account for the movement. As a result, the acquisition scan plane continuously or more likely passes through the region of interest.

Figure 2:
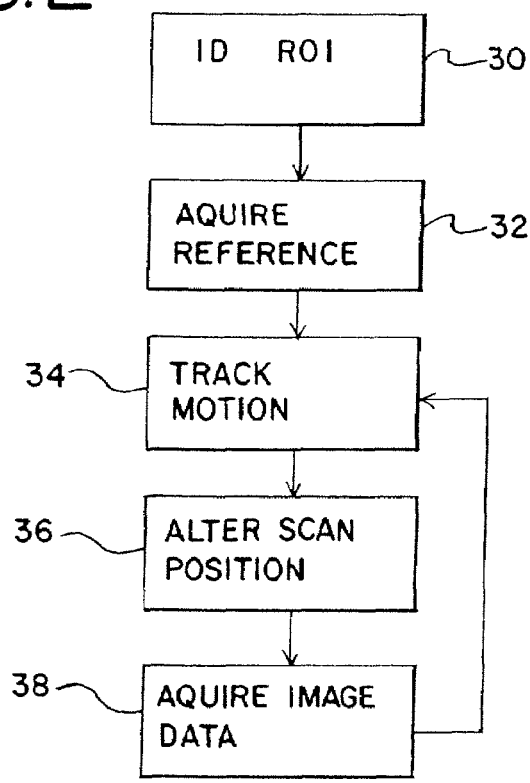
FIG. 2 is a flow chart diagram of a method for stabilizing an image plane in medical imaging in one embodiment.
Figure 3A:
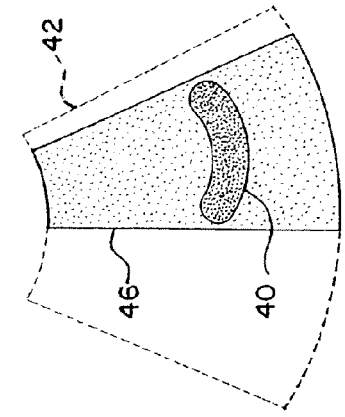
FIGS. 3A-3C are graphical representations of one embodiment for implementing the method of FIG. 2 for two-dimensional motion tracking.
Figure 3B:
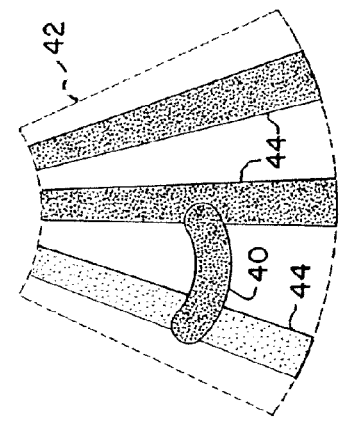
Figure 3C:
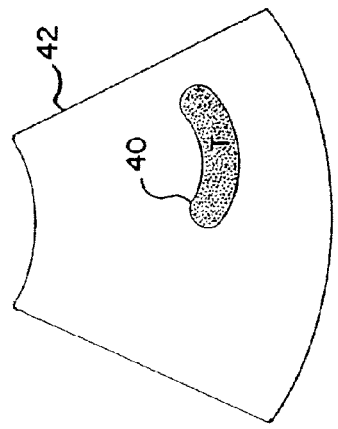
Figure 4A:
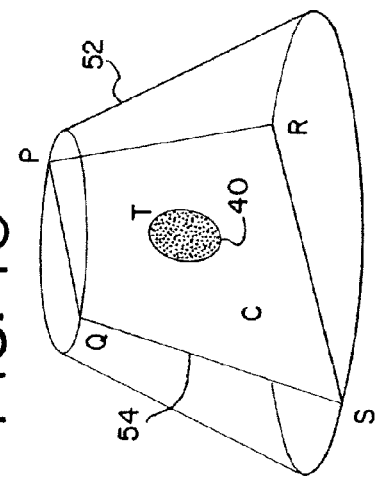
FIGS. 4A-4C are graphical representations representing another embodiment of FIG. 2 for three-dimensional motion tracking.
Figure 4B:
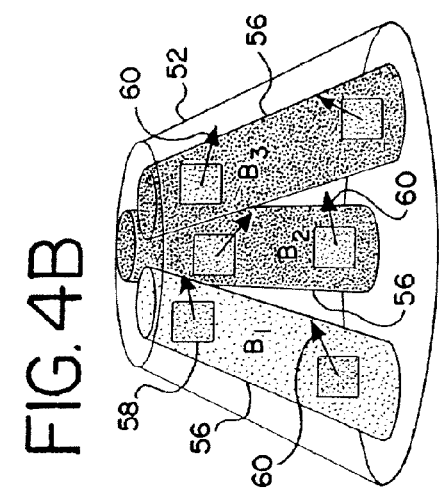
Figure 4C:
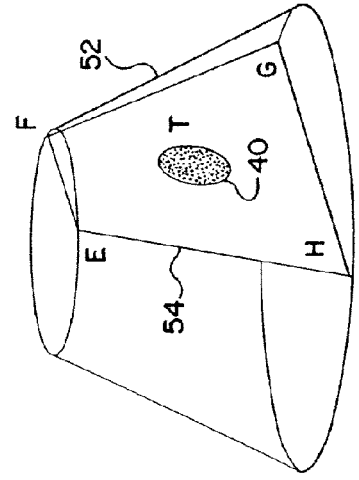

FIG. 2 shows one embodiment of a method for stabilizing imaging or an image plane within a volume in medical diagnostic ultrasound or other medical imaging. Different, additional or fewer acts are provided in other embodiments. The method of FIG. 2 is applicable to both two-dimensional and three-dimensional tracking. FIGS. 3A-3C show one embodiment of stabilizing a scan region in two dimensions. FIGS. 4A-4C show a graphic representation of an alternative embodiment of the stabilizing a two-dimensional scan region within a three-dimensional volume. FIG. 2 will be described with respect to both embodiments.

Referring to FIGS. 3A-3C and FIG. 2, a region of interest 40 is identified in act 30. The region of interest 40 is identified from a two-dimensional image of a region using a user input and/or automated detection. The region 42 represents a two-dimensional region for which the transducer is capable of scanning. The region of interest 40 is within the region 42. For example, an image representing the entirety of the region 42 or a subset of the region 42 is acquired.

Frame of reference data, such as data representing the entirety of the region 42 is acquired in act 32. Different or less sample density may be provided in acquiring the frame of reference than for subsequent imaging.

As represented in FIG. 3B, motion is tracked in act 34. A plurality of sub-regions 44, such as areas associated with a plurality of scan lines spaced throughout the region 42 are acquired. In alternative embodiments, the sub-regions are two-dimensional areas that extend less than an entirety of the depth of the region 42. Using speckle tracking or tracking of features (e.g., applying gradient processing and then tracking peak gradient locations), any motion of the sub-regions or subimages 44 relative to the reference is determined. For example, any of various constant or adaptive search processes are used to provide a best match or a sufficient match of each of the sub-regions 44 to the reference frame of data. A translation along two dimensions and a rotation for each of the subimages 44 is determined. In alternative embodiments, a translation along a single dimension, translation along two dimensions without rotation, or translation along a single dimension with rotation is used. The resulting translational and rotational vectors are combined, such as through averaging, to identify an overall motion. Since only sub-regions are scanned for tracking motion, the frame rate is now increased compared to scanning the whole volume for tracking.

As shown in FIG. 3C, a scan plane position is altered as a function of the tracked motion in act 36. The scan plane 46 is less than the entire spatial extent 42 possible by the transducer. The scan plane 46 is sized to just encompass the region of interest 40 or to include the region of interest 40 as well as additional information. As transducer movement relative to the region of interest 40 occurs, the scan plane 46 is positioned to scan a region of interest 40 based on the tracked motion.

In act 38, image data is acquired based on the shifted acquisition scan plane position. Since the scan plane 46 is shifted to account for motion, the region of interest 40 appears in the displayed image at a same location for each subsequent image regardless of motion between the region of interest 40 and the transducer 12. For example, the region of interest 40 shifts within the region 42 as shown in FIG. 3A as opposed to FIG. 3B. By shifting the scan plane 46, the region of interest 40 is then moved by the estimated motion amount in a reverse direction and shown to the user as the region 46 shown in FIG. 3C. The region of interest 40 appears to be stabilized or stationary and is included within each of the images. Acts 34, 36 and 38 are repeated for subsequent images without requiring further acquisition of an entire reference frame of data. In alternative embodiments, an entire frame of reference data may be subsequently acquired.

FIGS. 4A-4C and 2 represent a similar process for positioning a scan plane in a three-dimensional region 52 as opposed to the two-dimensional region 42 of FIGS. 3A-C. The three-dimensional region 52 corresponds to a volume that is a subset or the entirety of the volume that the transducer is operable to scan. As shown in FIG. 4A, the volume region 52 is conical but may be pyramid-shaped, cylindrical, or other shapes in other embodiments. The volume region 52 corresponds to electric steering of a two-dimensional array in one embodiment. The steering is at any of various angles, such as a normal through to 45 degrees away from normal. Other angles may be used.

In act 30, the region of interest 40 is identified. The user moves the transducer relative to the patient or causes the system to move the scan plane 54 to find the region of interest 40. For example, a two-dimensional region is scanned with ultrasound energy. As represented in FIG. 4A, the two-dimensional region is the plane EFGH within the volume region 52. In one embodiment, the plane 54 is positioned at a center of the transducer array, but may be positioned any where in any orientation within the volume region 52. In alternative embodiments, a three-dimensional representation is generated for identifying the region of interest 40.

Once an image includes the desired region of interest 40, the user inputs information designating the region of interest 40 within the region 52. For example, the user identifies the region of interest by tracing, by selecting two or more points, by selecting a point, by automatic border detection, automatic segmentation or by other now known or latter developed techniques. Based on the position of the scan plane 54 relative to the transducer 12 and the position of tissue designated within the image, the system 10 determines the spatial location of the region of interest 40 within the volume 52.

Once the region of interest 40 is identified, reference data is acquired in act 32. The entire three-dimensional volume is scanned. For example, a representative sample of the volume region 52 is obtained. A larger or smaller three-dimensional volume, such as associated with greater or lesser steering angles, may be scanned. The representative sample is acquired over the entire spatial extent in one embodiment, but may be acquired over lesser spatial extents in other embodiments. The entire spatial extent is based on an area of the two-dimensional transducer array and the steering angle. For example, the two-dimensional array used for acquiring data defines the entire spatial extent of the scan.

The representative sample is acquired over the entire or other spatial extent with a same or different scan line density than for subsequent imaging. Data representing at least portions of the three-dimensional volume are acquired for positions at least partially around the region of interest. A lesser line density, sample density or combinations thereof may be used. In one embodiment, the representative data is equally or evenly spaced throughout the volume region 52, but unequal or variations in sample or line density may be provided. In one embodiment, the data for the entire volume is acquired with a low resolution, such as using a low frequency or smaller aperture. Low resolution may result in a higher frame rate for scanning the entire spatial extent.

Once the region of interest 40 is identified and a frame of reference data in a known spatial relationship to the region of interest 40 is acquired, a two-dimensional area is repetitively scanned with the multi-dimensional transducer array. The two-dimensional area, such as the scan plane 54, is adaptively positioned within the volume region 52 as a function of tracked or detected motion. The two-dimensional area can be a C-Plane, B-Plane or any other variation of the above two planes, obtained by rotating C- or B-Planes. Instead of a 2D area, the transducer may also acquire a small 3D volume enclosing the region of interest, such as with two or more spatially distinct scan planes. By repositioning the two-dimensional area or the scan plane 54, the region of interest 40 is continually scanned despite relative movement between the region of interest 40 and the transducer 12.

In act 34, motion within the three-dimensional volume region 52 is tracked. The motion within the volume is repetitively detected for generating a plurality of images. Since the volume region 52 where motion is detected includes the two-dimensional scan plane 54 and associated region of interest 40, the detected motion indicates motion of the region of interest 40 within the volume region 52.

Motion is detected by comparing data acquired at different times, such as comparing each subsequently acquired set of data with the reference frame of data acquired in act 32. Rather than acquiring data representing the entire volume region 52, such as performed in act 32, a lesser amount of data is acquired to maintain higher frame rate. For example, acoustic energy is transmitted to three sub-regions of the three-dimensional volume region 52 without acquiring data for the entire three-dimensional volume region 52. In one embodiment, two of the sub-regions are along a same set of scan lines. More than three sub-regions along the same or different scan lines may be used. The data is acquired using fewer scan lines than performed for acquiring the reference information in act 32. As shown in FIG. 4B, three sets of scan lines 56 are transmitted at different angles and locations within the volume region 52. In one embodiment, each set of sub-regions includes nine adjacent scan lines, but sets of spaced scan lines, sparse scan lines, a greater number of scan lines or a fewer number of scan lines may be used. In one embodiment, each of the sets of scan lines 56 is of a same or similar scan line density, but different densities may be provided. In one embodiment, the scan line density and scan line positions for each of the sets of scan lines 56 are the same density and scan lines for a sub-volume used to acquire the reference frame data, but different densities or scan line positions may be used.

Acquisition parameters for obtaining data for motion tracking are the same or different than used for acquiring the reference information. In an alternative embodiment, acquisition of the tracking data is adaptive. For example, the size of each beam, the number of beams or other acquisition parameter is adjusted as a function of a previous motion estimate, the variance associated with the motion estimate or a measure of a tissue rigidity. For large variance motion estimates or low tissue rigidity, the beam size is increased or the number of beams is increased. The acquisition parameters may also be updated as a function of a change in acquisition parameters for imaging. For example, the user selects a different center frequency, aperture, F number, depths of imaging or other imaging parameter. The same parameter is altered for obtaining a tracking data. The same parameter is used for both tracking and imaging. In alternative or additional embodiments, different imaging parameters are used for tracking than for imaging.

Data associated with a cubed region at two or more different depths along each of the sets of scan lines 56 is used for comparison and motion detection. As shown in FIG. 4B, six tracking regions 58 are obtained. Additional or fewer sub-regions 58 may be used. In alternative embodiments, one or three or more sub-regions within each of the sets of scan lines 56 are used. While data representing cubes are acquired in one embodiment, data representing any of other various one, two or three-dimensional shapes may be used. In another embodiment, the data along the entire depth of each of the sets of scan lines 56 is used for motion detection. By acquiring data in only sub-regions 58 or along the sets of scan lines 56, a substantially lesser portion of the volume region 52 is scanned than is performed for acquiring the reference information or for scanning an entire volume. For example, 50 percent fewer scan lines are acquired as compared to scanning the entire volume 52 with a same density. A greater or lesser percentage may be provided. As a result, the sub-volumes also represent a substantially less total volume than the entire three-dimensional volume region 52.

The motion vectors 60 are determined by tracking each cube using speckle correlation. A high pass filter or other filtering and acquisition parameters are selected to best identify or provide speckle information. In alternative embodiments, a spatial gradient is applied to the data to identify one or more features within each sub-region 58. Easily identified landmarks, such a cystic areas, blood vessels or highly echogenic specular targets are tracked instead of tracking pixels within a sub-volume for speckle correlation. In another embodiment, the sub-regions 58 are adaptively placed prior to acquisition by identifying features within the reference frame of data acquired in act 32. Filtering or other techniques in addition to or as an alternative to a spatial gradient function may be used to identify one or more features. A feature pattern or volume around an identified single feature for each sub-volume 58 is identified. Filtering or other functions may be used in addition to or as an alternative to the spatial gradient for identifying a tracking feature.

A motion vector 60 is determined for each of the sub-volumes 58. For example, a direction, a magnitude or both a direction and a magnitude of the motion are determined by comparing the data from each of the sub-volumes 58 with the reference data acquired in act 32. In one embodiment, a translation within three dimensions is determined without determining rotation. The amount and direction of translation of the sub-volume 58 relative to the volume region 52 indicates a motion vector 60. Data responsive to the grouped sets of beams is used to determine the direction and magnitude of motion of the volume region 52 relative to the transducer. A minimum sum of absolute differences, cross correlation, or other now known or latter developed correlation is used to match the data for the sub-volumes 58 with the referenced data. Correlation is performed using data prior to detection, data after detection but prior to scan conversion, data after scan conversion, display image data, or other data. Any of various search patterns involving translating and/or rotating the data representing the sub-volumes 58 relative to the referenced data is used to identify a best match. A coarse search followed by a fine search, a search adapted to expected motion, a size of the region to be searched adapted to previous amounts of motion, or other adaptive or efficient search techniques may be used.

The same reference data is used to compare to each subsequently acquired set of data representing sub-regions 58. In alternative embodiments, data representing a subsequently acquired sub-volume 58 is compared to data from a previously acquired sub-volume in a same general area. Given minimal amount of motion, the motion vector may be small enough to track from one sub-volume to a subsequently acquired sub-volume without comparison to the reference frame of data.

As an alternative to finding individual motion vector 60 for each sub-volume, the sub-volumes are translated and/or rotated as a group to find a single motion vector. Where two or more different motion vectors are detected for a given time, a least squares fit, an average, or other combination of the motion vectors is used to calculate a single transformation indicating motion of the transducer 12 relative to the volume region 52. Rigid body motion is assumed for each sub-volume, but warping or other techniques may be used to account for tissue deformation. Translations in three dimensions and rotations about the three dimensions are determined using a least squares fit, such as determined from using six separate motion vectors shown in FIG. 4B. U.S. Pat. No. 6,306,091, the disclosure of which is incorporated herein by reference, discloses various techniques for identifying a rigid body transformation from a plurality of vectors. The motion tracking, subvector or global vector techniques disclosed in the '091 patent are extended to three-dimensional processing. The resulting rigid body transformation represents six degrees of freedom, such as a translation in an X, Y and Z dimensions as well as rotation about each of the dimensions. In alternative embodiments, fewer degrees of freedom or motion associated with only translation, only rotation or a subset of the six degrees of freedom is provided.

Since the characteristics of the speckle may change as a function of position within the volume region 52, one or more tracking parameters are adjusted as a function of a position of the tracking location within the region 52. For example, as the speckle is positioned deeper and deeper within the region 52, diffraction results in larger speckle. Element factor or other factors may change as a position of depth, steering angle or other location within volume region 52. The correlation, cross correlation, minimum sum of differences or other matching function is altered based on the position. Through example, a warping, such as a one-, two- or three-dimensional expansion or contraction of the data is performed as part of the correlation operation as a function of the position of the tracking location. By spatially expanding or contracting the data, the data more likely matches the reference data. Other warping may be used. Differences in thresholds for identifying a best or sufficient match, differences in an algorithm apply to track motion or other tracking parameters are altered as a function of the location. Alternatively, the tracking parameters are the same regardless of position. Other types of transformations, besides rigid body transformation may be estimated between the reference data set and the subsequent sub regions. One such technique is image morphing as described in U.S. Pat. No. 6,659,953 (application Ser. No. 10/251,044) for Morphing Diagnostic Ultrasound Images for Perfusion Assessment, the disclosure of which is incorporated herein by reference.

In act 36, the position of the acquisition scan plane 54 is automatically altered relative to the transducer 12 as a function of the detected motion. FIG. 4C shows transformation of the acquisition scan plane 54 to account for the detected or estimated motion. By translating and rotating the acquisition scan plane 54, subsequent acquisition along the scan plane 54 more likely scans the region of interest 40. The acquisition scan plane 54 is maintained at a position to intersect the region of interest 40 over time. The position of the acquisition scan plane 54 is altered within the three-dimensional volume region 52 to account for relative motion between the region of interest 40 and the transducer 12. The motion tracking provides information on the position of the region of interest 40 within the volume region 52 relative to the transducer 12. The acquisition scan plane (i.e., the transmission and/or reception plane) is adaptively repositioned, altered or updated. The two-dimensional area of the acquisition scan plane is positioned within the volume as a function of and in response to the detected motion and the region of interest 40. As shown in FIG. 4C, the acquisition scan plane 54 is positioned in a plane QPRS different than the EFGH plane of FIG. 4A as a function of the motion vectors 60 shown in FIG. 4B. The region of interest 40 moves in a direction opposite to the detected motion.

Using electronic or mechanical steering, the acquisition scan plane 54 is translated and/or rotated, such as translating and rotating within the six degrees of freedom. In alternative embodiments, the acquisition scan plane 54 is translated and maintained at the same angle relative to the normal to the array or not rotated. Where a two-dimensional transducer is used, six degrees of freedom may be provided for positioning the acquisition scan plane 54. Fewer degrees of freedom may be provided for other multi-dimensional or two-dimensional arrays. The scan plane 54 is adaptively positioned using one or more degrees of freedom to more likely scan the region of interest 40. Where motion is indicated beyond the original extent of the volume 52 or beyond the ability to acquire a sufficiently large acquisition scan plane 54, stabilized imaging is ceased, imaging without the stabilization described herein is performed or the process returns to acquire a reference frame of data in act 32 for a new extent of the volume region 52. In another embodiment, the reference frame of data is acquired for every N frames of data containing the region of interest, where N is a number such as 10. Other values may also be used for N.

In act 38, image data is acquired. Acoustic energy is electronically or mechanically steered across the acquisition scan plane 54 in any of now known or later developed formats, such as sector, vector, linear or as a plane wave. The data from acoustic echoes represents the tissue intersected within the acquisition scan plane 54. Received data is beamformed, image processed and used to generate a two-dimensional or three-dimensional display. The region of interest 40 is represented in the image due to the shift in the scan plane position. In alternative embodiments, spectral Doppler display associated with a range gate position or point, continuous wave Doppler display associated with a line, or M-mode display associated with a line are generated from a point or line within the scan plane 54. The point or line are tracked and adaptively positioned.

The motion tracking of act 34, the acquisition scan plane position alteration of act 36 and the acquisition of image data of act 38 are repeated over time such that the two-dimensional acquisition scan plane 54 is adaptively positioned to intersect the region of interest over time. The adaptively positioned acquisition scan planes are repetitively scanned for generating images. Upon viewing a sequence of images, the user perceives the region of interest 40 as being stationary or stabilized. The region of interest 40 is less likely to fade out of the images due to the adapted positioning of the scan plane 54. The acquisition scan plane 54 is maintained in a position to intersect the region of interest 40 during multiple acquisitions accounting for relative motion of the transducer 12 to the tissue.

By acquiring image data from the two-dimensional area of the acquisition scan plane 54 or a one-dimensional line or point, rapid or high frame rate imaging is provided. Since the motion tracking uses sub-volumes, the affect on frame rate is greatly reduced as opposed to tracking using the entire volume region 52. As a result, real time or substantially real time two-dimensional imaging is provided with three-dimensional motion tracking.

Further stabilization is provided by shifting the resulting two-dimensional images as a function of an initial position of the region of interest 40. Adaptive positioning of the acquisition scan plane 54 results in the region of interest 40 being continually imaged. The region of interest 40 may also or alternatively be shifted within the display two-dimensional image by translation along one or two dimensions and/or rotation to maintain further stabilization. For example, as the transducer shifts to the left relative to the tissue, the region of interest 40 may appear to shift to the left within resulting images. The region of interest 40 is tracked or the shift is accounted for in the display two-dimensional image. In one embodiment, the shift occurs to the image data in range and azimuth. In another embodiment, the acquisition scan plane 54 extends only over a portion of the width of the volume region 52 accessible by the transducer 12. As a result, the positioning of the acquisition scan plane automatically shifts the region of interest 40 in the displayed image. Where tissue is compressed due to additional pressure from the transducer 12 or extended due to a release of pressure, the region of interest 40 may appear to shift upwards or downwards on the image. Either through changing a depth associated with the acquisition scan plane 54 or by shifting the resulting image data upwards or downwards, the region of interest 40 is maintained in the same location on the display.

A further shift in the acquisition scan plane position 54 may be performed as a function of time. For example, the difference in time between acquisition of the data used for tracking motion and the acquisition of data used for generating an image is considered. A velocity, acceleration or both velocity and acceleration are determined. The temporal difference is used with the velocity or acceleration information to determine an additional shift.

The tracking of the imaging plane is used for any B-mode, Doppler, M-mode, spectral Doppler, continuous wave Doppler, harmonic, contrast agent imaging or other imaging. Other applications may benefit from tracking the position of the acquisition scan plane 54 in three-dimensional volume region 52. For example, tumor perfusion using contrast agents or other radiology-based contrast quantification is performed. Contrast agent quantification may also be performed for myocardial perfusion or other cardiology applications. Triggered imaging of the heart is provided so that the resulting images are acquired at a same time during a heart cycle. Alternatively, warping or other non-rigid motion is accounted for throughout the heart cycle. Another application is a biopsy or surgical guidance. Better guidance may be provided by maintaining the scan plane in position relative to the region of interest. Yet other applications are cardiovascular quantitative measurements, such as vascular measurements of carotid plaque assessment, pulsatility, aortic aneurism or others.

In one embodiment, the acquisition scan plane is used for acquiring Doppler information for both Doppler and B-mode information. The motion is tracked using B-mode or other information. Any of various combinations of using the same or different data for tracking and imaging may be used. By stabilizing the scan plane position relative to the region of interest 40, more aggressive persistence for Doppler imaging may be used with no or minimal decrease in resolution. Vessel structure reconstruction may also be improved. Other high persistence imaging, such as contrast agent imaging to identify microvascular structures, may be improved.

By reducing the artifacts due to patient or sonographer motion for two-dimensional imaging, work flow may be improved, reducing the amount of acquisition data and the amount of acquisition time. Off-line motion tracking processing is eliminated by providing for a tracking and imaging described above in real time or while a patient is being scanned during an imaging session. Real time imaging is provided due to the reduced or minimal impact of acquiring motion information using sub-volumes. Motion tracking is performed in three dimensions without having to acquire consecutive full three-dimensional volume representations of data.

As an alternative to two-dimensional imaging of a region of interest, stabilization of the acquisition scan plane is used for acquiring a three-dimensional set of data. Using electronic steering, the scan plane is purposefully positioned at different locations within the volume region 52. To provide regular spacing of the acquisition scan plane for a more uniform density of samples throughout the three-dimensional region, motion of the transducer 12 relative to the tissue is accounted for as discussed above. The acquisition scan plane position is adjusted as a function of both the motion and the intended displacement for three-dimensional data acquisition.

While the invention has been described above by reference to various embodiments, it should be understood that many changes and modifications can be made without departing from the scope of the invention. For example, the same firings and data are used for both tracking and imaging. As another example, one or more sub-volumes 58 for tracking are positioned within, as parts of, or overlapping with the region of interest. It is therefore intended that the foregoing detailed description be regarded as illustrative rather than limiting, and that it be understood that it is the following claims, including all equivalents, that are intended to define the spirit and the scope of this invention.

We claim:

1. A method for stabilizing a scan plane within a volume in medical diagnostic ultrasound imaging, the method comprising:
   (a) identifying a region of interest;
   (b) acquiring data representing at least portions of a three-dimensional volume positioned at least partly around the region of interest;
   (c) acquiring data representing sub-volumes of the three-dimensional volume, (c) using fewer scan lines than (b);
   (d) comparing the data representing the sub-volumes with the data representing at least the portions of the three-dimensional volume;
   (e) detecting motion of the region of interest within the three-dimensional volume as a function of (d);
   (f) positioning a two-dimensional scan plane within the three-dimensional volume as a function of the region of interest and the detected motion of the region of interest such that the two-dimensional scan plane is maintained at the region of interest in the volume despite the motion; and
   (g) acquiring a two-dimensional image responsive to the two-dimensional scan plane.

2. The method of claim 1 wherein (b) comprises acquiring data representing an entire spatial extent of the three-dimensional volume, the entire spatial extent being based on an area of a two-dimensional transducer array used for (b), (c) and (g), wherein (c) comprises acquiring the data representing sub-volumes of the three-dimensional volume, the sub-volumes together being substantially less than the three-dimensional volume.

3. The method of claim 1 wherein comparing and detecting comprise tracking the motion, and wherein positioning comprises automatically altering the two-dimensional scan plane position relative to a transducer as a function of the motion.

4. The method of claim 1 wherein positioning comprise positioning the two-dimensional scan plane position such that the two-dimensional image is of the region of interest.

5. The method of claim 1 wherein comparing comprises performing a cross-correlation or a sum of absolute differences.

6. The method of claim 1 wherein (b) and (c) comprise acquiring at different times.

7. The method of claim 1 further comprising:
   scanning the region with ultrasound energy;
   wherein identifying comprises receiving input designating the region of interest within the region.

8. The method of claim 1 wherein acquiring data representing the sub-volumes comprises scanning a representative sample of the entire three-dimensional volume.

9. The method of claim 1 wherein acquiring data representing the sub-volumes comprises transmitting at least three grouped sets of beams spaced apart within the three-dimensional volume, wherein detecting comprises determining a direction and a magnitude of motion from data responsive to the at least three grouped sets of beams for each of the at least three grouped sets of beams, and wherein positioning comprises altering the two-dimensional scan plane positioning as a function of the at least three directions and at least three magnitudes.

10. The method of claim 1 further comprising identifying at least one feature within the three-dimensional volume, wherein comparing and detecting comprise tracking motion of the at least one feature.

11. The method of claim 1 wherein comparing and detecting comprise tracking speckle or a spatial gradient.

12. The method of claim 1 further comprising:
   (c) adjusting a tracking parameter for comparing and detection as a function of a position of a tracking location within the three-dimensional volume.

13. The method of claim 1 wherein acquiring the data representing sub-volumes comprises obtaining the data in response to different acquisition parameters than used for acquiring the two-dimensional image.

14. The method of claim 1 further comprising:
   (h) repeating (c), (d), (e), (f) and (g) over time such that the two-dimensional scan plane is adaptively positioned through the region of interest over time.

15. The method of claim 14 wherein repeating the positioning comprises translating and rotating the two-dimensional scan plane to the region of interest.

16. The method of claim 14 wherein comparing and detecting comprise tracking the motion within the three-dimensional volume, and wherein repeating the positioning comprises altering the two-dimensional scan plane position relative to the transducer, the transducer being a multi-dimensional array of elements, the alteration maintaining the two-dimensional scan plane at the region of interest within the three-dimensional volume over time.

17. The method of claim 14 wherein acquiring data representing sub-volumes is repeated without acquiring data for the entire three-dimensional volume.

18. The method of claim 14 wherein repeating the positioning comprises automatically altering the two-dimensional scan plane relative to a transducer as a function of the motion.

* * * * *